(12) United States Patent
Akagawa (10) Patent No.: US 8,452,203 B2
(45) Date of Patent: May 28, 2013

(54) IMAGE FORMING APPARATUS WITH AN AIR PURIFIER

(75) Inventor: Yuhi Akagawa, Osaka (JP)

(73) Assignee: Sharp Kabushiki Kaisha, Osaka-Shi (JP)

( * ) Notice: Subject to any disclaimer, the term of this patent is extended or adjusted under 35 U.S.C. 154(b) by 269 days.

(21) Appl. No.: 12/899,180

(22) Filed: Oct. 6, 2010

(65) Prior Publication Data
US 2011/0085819 A1    Apr. 14, 2011

(30) Foreign Application Priority Data
Oct. 13, 2009   (JP) ................................. 2009-235968

(51) Int. Cl.
G03G 21/20   (2006.01)
G03G 21/00   (2006.01)

(52) U.S. Cl.
USPC .............................. 399/98; 399/92

(58) Field of Classification Search
USPC .............................. 399/92, 93, 98
See application file for complete search history.

(56) References Cited

U.S. PATENT DOCUMENTS

| | | | |
|---|---|---|---|
| 7,136,613 B2 * | 11/2006 | Sato et al. ..................... | 399/299 |
| 7,313,341 B2 * | 12/2007 | Matsusaka ...................... | 399/88 |
| 7,486,904 B2 * | 2/2009 | Sato et al. ...................... | 399/92 |
| 2010/0183327 A1 * | 7/2010 | Kajiwara et al. ................ | 399/93 |

FOREIGN PATENT DOCUMENTS

| | | |
|---|---|---|
| JP | 2004-233618 | 8/2004 |
| JP | 2005-004144 | 1/2005 |
| JP | 2005-099505 | 4/2005 |

* cited by examiner

Primary Examiner — Joseph S Wong
(74) Attorney, Agent, or Firm — Nixon & Vanderhye P.C.

(57) ABSTRACT

In an image forming apparatus, exhaust fans of a ventilation device and an intake port of an air purifier are provided on side wall portions respectively that are opposite each other in a main casing of the image forming apparatus, and the exhaust fans of the ventilation device are provided in a location higher than the intake port of the air purifier. With this configuration, silicone that is discharged from the exhaust fans of the ventilation device is almost never suctioned into the intake port of the air purifier, such that almost none of this silicone adheres to a discharging electrode of the ion generator, and an ion generating efficiency of the ion generator can be maintained over a long period without dropping.

12 Claims, 6 Drawing Sheets

IMAGE FORMING APPARATUS WITH AN AIR PURIFIER

BACKGROUND OF THE INVENTION

This application claims priority under 35 U.S.C. §109(a) on Patent Application No. 2009-235968 filed in Japan on Oct. 13, 2009, the entire contents of which are herein incorporated by reference.

The present invention relates to image forming apparatuses such as copiers, printers, and fax machines.

Electrophotographic apparatuses are an example of this type of image forming apparatus. In electrophotographic apparatuses, a toner image is formed on a surface of a photosensitive drum by forming an electrostatic latent image on the surface of the photosensitive drum, then developing the electrostatic latent image on the surface of the photosensitive drum using toner, and the toner image is transferred from the photosensitive drum to a recording paper and fixed onto the recording paper by applying heat and pressure to the recording paper.

Image forming apparatuses such as these are essential office automation appliances and are installed in most offices, moreover they are also becoming widespread in homes and hospitals.

In this regard, electrophotographic image forming apparatuses have sometimes caused discomfort to many people in offices, homes, and hospitals and the like since they produce exhaust gases and the like during the process of forming a toner image on the recording paper.

For this reason, in JP 2005-4144A for example, components such as a ventilation fan, a negative ion generating portion, a positively charged filter, and an ozone filter are provided inside an image forming apparatus, and while the inside of the image forming apparatus is ventilated by the ventilation fan, dust and mold and the like that have entered from outside are negatively charged by the negative ion generating portion and these are adsorbed and removed by the positively charged filter, or gases or the like inside the image forming apparatus are reduced by an ozone removal filter, thereby discharging clean air to the outside. Accordingly, with the conventional technology of JP 2005-4144A, it is possible to remove dust and mold and the like that have entered from outside the image forming apparatus, and to reduce gases inside the image forming apparatus to release clean air externally.

However, with the conventional technology of JP 2005-4144A, despite being able to purify the air in a room, the negative ion generating portion is a structure that is exposed to gases inside the image forming apparatus, and therefore the ion generating efficiency of the negative ion generating portion is reduced at an early stage. This is considered to be because the gases inside the image forming apparatus contain silicone that is mixed with toner powder and release agents for releasing recording papers, and this silicone adheres to components such as the discharging electrodes of the negative ion generating portion, which reduces the insulation of the negative ion generating portion.

Accordingly, the present invention was devised to address the above-described issues, and it is an object thereof to provide an image forming apparatus that has an inbuilt air purifier having an ion generator, and that is capable of maintaining the ion generating efficiency of its ion generator without reductions over a long period while purifying the air in a room.

SUMMARY OF THE INVENTION

In order to address these issues, an image forming apparatus according to the present invention is provided with a ventilation device that ventilates air inside the image forming apparatus, wherein an air purifier having an ion generator is provided isolated inside the image forming apparatus, and air outside the image forming apparatus is suctioned and purified by the air purifier, with purified air being discharged, and an intake port of the air purifier that suctions air is provided in a location apart from an exhaust port of the ventilation device.

With the present invention, the air purifier having the ion generator is provided isolated inside the image forming apparatus, and therefore the ion generator is not exposed to the gases inside the image forming apparatus. Furthermore, the intake port of the air purifier that suctions air is provided in a location apart from the exhaust port of the ventilation device, and therefore the air discharged from the exhaust port of the ventilation device, namely air containing exhaust gases of the image forming apparatus, almost never flows to the intake port of the air purifier, and is almost never suctioned into the intake port of the air purifier. For this reason, gas constituents of the image forming apparatus almost never adhere to the discharging electrodes of the ion generator, and an ion generating efficiency of the ion generator can be maintained over a long period without dropping.

An ion generator is preferable that simultaneously generates and emits positive ions and negative ions. Positive ions and negative ions can effectively remove airborne microbes in the air.

In the above-described configuration, for example, the intake port of the air purifier and the exhaust port of the ventilation device may be provided in mutually different wall portions respectively of the main casing of the image forming apparatus. More specifically, since in general the main casings of image forming apparatuses are substantially six sided solid shapes, the intake port of the air purifier and the exhaust port of the ventilation device may be provided at the wall portions of two mutually different surfaces of the six surfaces of the six sided structure. In this way, the intake port of the air purifier can be provided reliably apart from the exhaust port of the ventilation device.

Furthermore, the intake port of the air purifier and the exhaust port of the ventilation device may be provided in wall portions respectively that are opposite each other of the main casing of the image forming apparatus. In this case, the intake port of the air purifier and the exhaust port of the ventilation device are arranged at ends of the main casing of the image forming apparatus, and therefore it is extremely difficult for air that is discharged from the exhaust port of the ventilation device to be suctioned into the intake port of the air purifier.

Furthermore, the intake port of the air purifier and the exhaust port of the ventilation device may be provided at a front surface side wall portion and a rear surface side wall portion of the main casing of the image forming apparatus. In this case, the intake port of the air purifier and the exhaust port of the ventilation device are arranged at ends of the main casing of the image forming apparatus, and therefore it is extremely difficult for air that is discharged from the exhaust port of the ventilation device to be suctioned into the intake port of the air purifier.

Furthermore, the intake port of the air purifier and the exhaust port of the ventilation device may be provided apart from each other below and above at one wall portion of the main casing of the image forming apparatus. The air that is ventilated by the ventilation device is warmed inside the image forming apparatus then discharged from the exhaust port of the ventilation device and rises outside the image forming apparatus. Thus, in the present embodiment, the intake port of the air purifier is arranged below, and the exhaust port of the ventilation device is arranged above, and therefore the air discharged from the exhaust port of the ventilation device is almost never suctioned into the intake port of the air purifier, which is below the exhaust port.

Furthermore, the intake port of the air purifier and the exhaust port of the ventilation device may be provided at end portion positions apart from each other at one wall portion of the main casing of the image forming apparatus. In this case, the air discharged from the exhaust port of the ventilation device can be inhibited from being suctioned into the intake port of the air purifier.

Furthermore, an exhaust port of the air purifier may be provided at a front surface side wall portion of the main casing of the image forming apparatus. In this case, the air discharged from the exhaust port of the air purifier can spread widely in the room, and airborne microbes in the air can be efficiently removed by the ions contained in this air.

Furthermore, a duct may be provided that protrudes above the image forming apparatus, and an exhaust port of the air purifier that discharges air is connected to the duct to discharge air via the duct to above the image forming apparatus. In this case, the air discharged from the exhaust port of the air purifier can spread widely in the room, and airborne microbes in the air can be efficiently removed by the ions contained in this air.

Furthermore, a paper feeding portion may be arranged at a bottom portion of the image forming apparatus, a paper discharge portion arranged above the paper feeding portion, and a printer portion that is arranged at an intermediate height between the paper feeding portion and the paper discharge portion, and that receives a recording paper from the paper feeding portion and forms an image on the recording paper, then discharges the recording paper to the paper discharge portion, and the air purifier may be arranged below the paper discharge portion. In this case, the air purifier can be arranged below the paper discharge portion. Currently, although the installation space for the air purifier is limited due to the compactness of the image forming apparatus, the above-described configuration easily enables an installation space for the air purifier to be secured below the paper discharge portion.

Furthermore, when the air purifier is arranged below the paper discharge portion, the air purifier is arranged partitioned adjacent to the printer portion, and is easily isolated from the ventilation device arranged near the printer portion. And it is also possible to provide the intake port of the air purifier and the exhaust port of the ventilation device near the wall portions respectively that are opposite each other in the main casing of the image forming apparatus, and the intake port of the air purifier and the exhaust port of the ventilation device can be provided at the wall portions respectively. In this case, it is not necessary to lengthen the air path of the air purifier to ensure the intake port is far from the exhaust port, and it is also unnecessary to increase the size of the air purifier, and thus increases in size of the image forming apparatus can be inhibited.

Furthermore, the air purifier may be provided with a filter for adsorbing silicone. In this case, the air purifier has a filter for adsorbing silicone, and therefore even if silicone is contained in the exhaust gases of the image forming apparatus and this silicone is suctioned into the intake port of the air purifier, the silicone is adsorbed by the filter for adsorbing silicone, and the silicone does not adhere to the discharging electrodes of the ion generator.

DESCRIPTION OF THE PREFERRED EMBODIMENTS

Hereinafter, embodiments of the present invention are described in detail with reference to the accompanying drawings.

Figure 1:
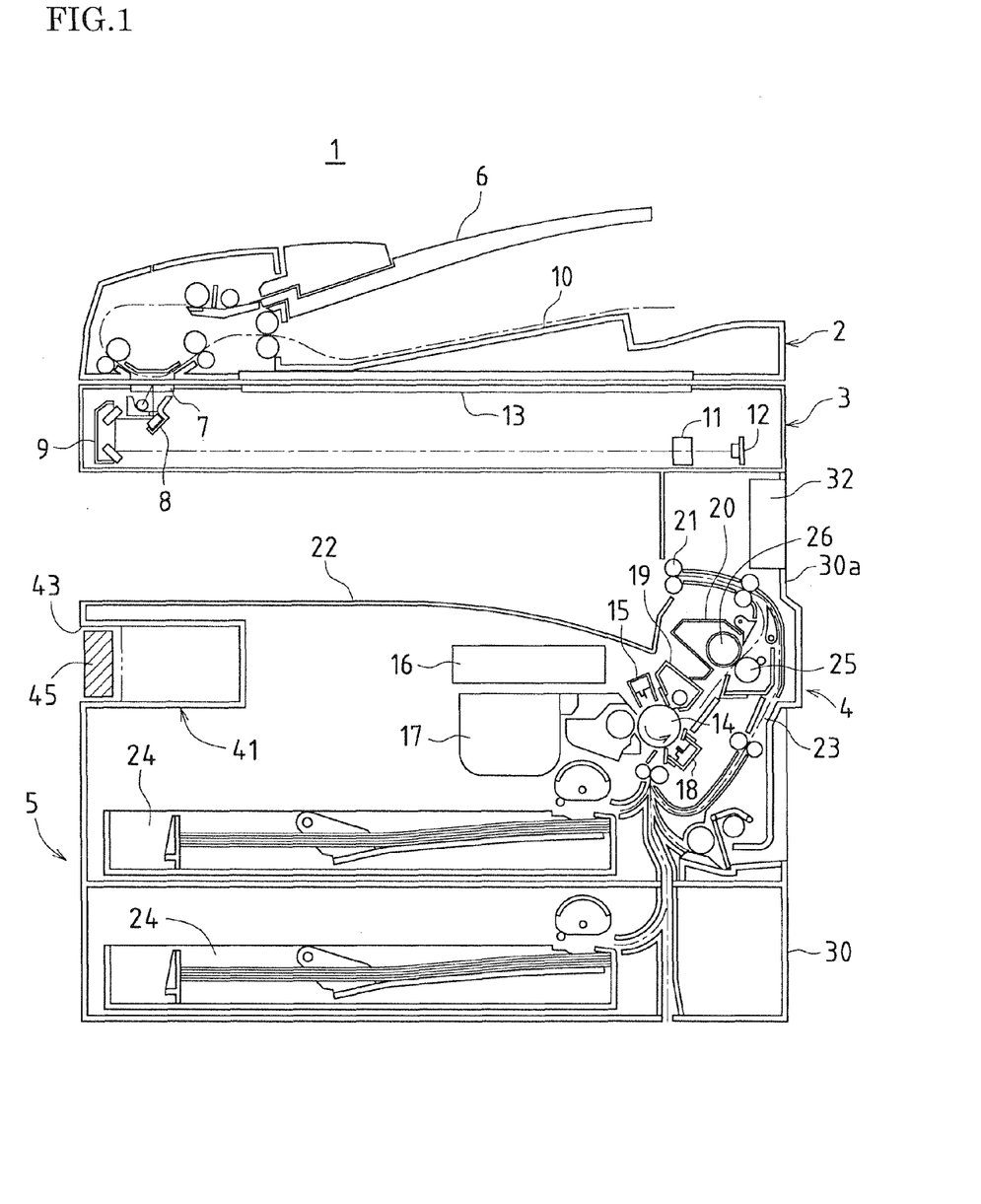
FIG. 1 is a cross-sectional view showing a first embodiment of an image forming apparatus according to the present invention.

FIG. 1 is a cross-sectional view showing a first embodiment of an image forming apparatus according to the present invention. An image forming apparatus 1 according to the present embodiment reads an original to obtain image data of the original or obtains image data received externally, and forms a monochrome image indicated by the image data on a recording paper, and its structure can be broadly divided into an original transport portion (ADF) 2, an original reading portion 3, a printer portion 4, and a paper feeding portion 5.

When at least one sheet of an original is set in an original setting tray 6 in the original transport portion 2, the original is withdrawn and transported from the original setting tray 6 sheet by sheet, and the original is guided and caused to pass in a sub scanning direction over a first platen glass 7 of the original reading portion 3, then the original is discharged to a discharge tray 10.

In the original reading portion 3, an optical unit, which is constituted by components such as first and second scanning portions 8 and 9, an imaging lens 11, and a CCD (charge coupled device) 12, is arranged under the first platen glass 7, and when an original passes in the sub scanning direction over the first platen glass 7, a front surface of the original is exposed by a light source of the first scanning portion 8, then reflected light from the front surface of the original is guided by mirrors of the first and second scanning portions 8 and 9 to the imaging lens 11, and an image of the front surface of the original is imaged onto the CCD 12 by the imaging lens 11. The CCD 12 repetitively reads in a main scanning direction the image of the front surface of the original and outputs image data that indicates the image of the front surface of the original.

Furthermore, it is possible to read an original that has been placed on a second platen glass 13. One back side of the original transport portion 2 is pivotably supported by a hinge (not shown in drawings) on one back side of the original reading portion 3, which is located below, and a front area of the original transport portion 2 can be opened and closed by being raised or lowered. When the original transport portion 2 is opened, the second platen glass 13 is uncovered, and an original can be placed on the second platen glass 13. In a state in which an original has been placed and the original transport portion 2 has been closed, the first and second scanning portions 8 and 9 move in the sub scanning direction while the front surface of the original on the second platen glass 13 is exposed by a light source of the first scanning portion 8, then the reflected light from the front surface of the original is guided to the imaging lens 11 by mirrors of the first and second scanning portions 8 and 9, and an image of the front surface of the original is imaged onto the CCD 12 by the imaging lens 11. At this time, the first and second scanning portions 8 and 9 move while maintaining a predetermined velocity relationship with each other, and a positional relationship of the first and second scanning portions 8 and 9 is constantly maintained such that an optical path length of the reflected light, which is from the front surface of the original, to the first and second scanning portions 8 and 9, then to the imaging lens 11, and the CCD 12, does not vary, and in this way a focus of the image of the front surface original onto the CCD 12 is always maintained accurately.

Image data outputted from the CCD 12 undergoes various types of image processing by an arithmetic circuit such as a microcomputer and is then outputted to the printer portion 4.

Accordingly, the original reading portion 3 makes combined use of both a transported original method, in which originals are transported over the first platen glass 7, and a secured original method, in which the original is placed on the second platen glass 13 and the first and second scanning portions 8 and 9 are moved.

A photosensitive drum 14 is arranged substantially centrally in the printer portion 4, and a charging unit 15, an optical scanning unit 16, a developer unit 17, a transfer unit 18, and a cleaning unit 19 are arranged there around.

The charging unit 15 uniformly charges the surface of the photosensitive drum 14. The optical scanning unit 16 inputs image data then scans an optical beam on the uniformly charged surface of the photosensitive drum 14 while modulating the intensity of the optical beam in response to the image data, thereby writing an electrostatic latent image on the surface of the photosensitive drum 14. The developer unit 17 uses toner to develop the electrostatic latent image on the surface of the photosensitive drum 14, thereby forming a toner image on the surface of the photosensitive drums 14.

When a recording paper is transported in by the paper feeding portion 5, the transfer unit 18 transfers the toner image on the surface of the photosensitive drum 14 onto the recording paper while the recording paper is transported sandwiched between itself and the photosensitive drum 14. The cleaning unit 19 removes any toner that is residual on the surface of the photosensitive drum 14, thereby enabling a new toner image to be recorded on the surface of the photosensitive drum 14.

A fixing device 20 is arranged at an upper area of the printer portion 4. The fixing device 20 sandwiches the recording paper on which the image has been transferred between a heating roller 25 and a pressure roller 26, thereby applying heat and pressure to the recording paper and causing the toner image that has been transferred onto the recording paper to become fixed.

The recording paper is transported upward by transport rollers then discharged from discharge rollers 21 to a discharge tray 22.

Furthermore, in a case where an image is to be formed on both sides of the recording paper, the recording paper is reverse transported in a reverse direction by the discharge rollers 21, then transported again to a reverse transport path 23 where its front and back surfaces are turned over and transported again to the printer portion 4, then a toner image is transferred onto that back surface and fixed. Then the recording paper is discharged from the discharge rollers 21 to the discharge tray 22.

The paper feeding portion 5 is provided with paper feeding cassettes 24, and recording papers are separated and supplied sheet by sheet from these paper feeding cassettes 24. The recording paper is fed between the photosensitive drum 14 and the transfer unit 18, and a toner image on the photosensitive drum 14 is transferred to the recording paper.

Next, detailed description is given of a configuration of a ventilation device and an air purifier in the image forming apparatus 1 according to the present embodiment.

Figure 2:
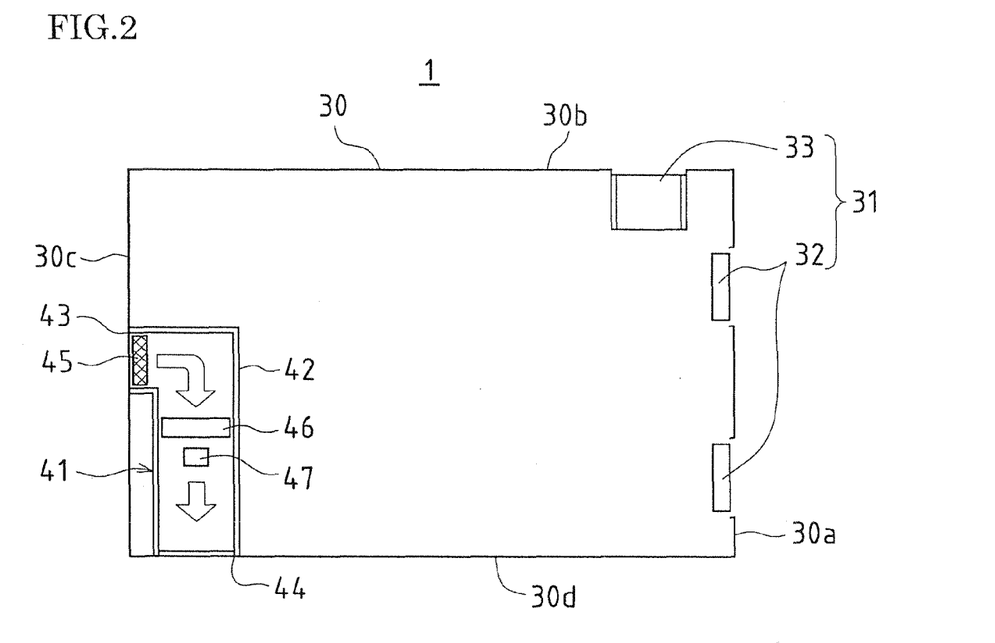
FIG. 2 is a schematic view showing a ventilation device and an air purifier in an image forming apparatus as viewed from above in the image forming apparatus of FIG. 1.

FIG. 2 is a schematic view showing a ventilation device and an air purifier in the image forming apparatus 1 as viewed from above. The image forming apparatus 1 has a main casing 30, which is a substantially six sided solid shape. A ventilation device 31 is provided with two exhaust fans 32, which are arranged on a side wall portion 30a of the main casing 30, and an intake opening 33, which is arranged on a rear surface side wall portion 30b of the main casing 30.

Each of the exhaust fans 32 is provided with components such as a ventilation fan, a motor for rotational drive of the ventilation fan, and a filter, and air inside the image forming apparatus 1 is discharged to the outside through the filter due to the rotational drive of the ventilation fan. Consequently, each of the exhaust fans 32 fulfills a function of an exhaust port that forcibly discharges the air inside the image forming apparatus 1. The exhaust fans 32 are disposed above the fixing device 20 (see FIG. 1) so as to be capable of efficiently exhausting hot air that rises from near the heating roller 25 of the fixing device 20.

Furthermore, the intake port 33 is a simple opening formed in the rear surface side wall portion 30b of the main casing 30. When air inside the image forming apparatus 1 is discharged by the exhaust fans 32, air from outside is suctioned into the image forming apparatus 1 through the intake port 33 due to this. The intake port 33 is arranged below the printer portion 4, that is, near a bottom portion of the image forming apparatus 1, so that the outside air suctioned in from here reaches to the exhaust fans 32 via the printer portion 4.

During operation of the image forming apparatus 1, an internal temperature of the image forming apparatus 1 is detected by a sensor, and when the detected internal temperature exceeds a fixed value, the motors of the exhaust fans 32 are rotationally driven. Due to the rotational drive of the motors of the exhaust fans 32, their ventilation fans rotate and discharge the air inside the image forming apparatus 1, while on the other hand, outside air is suctioned into the image forming apparatus 1 through the intake port 33, thereby ventilating inside the image forming apparatus 1. As a result, rises in the internal temperature of the image forming apparatus 1 are inhibited. Furthermore, when the internal temperature detected by the sensor falls below the fixed value, the motors of the exhaust fans 32 are stopped.

Furthermore, not only are rises in the internal temperature of the image forming apparatus 1 inhibited due to the ventilation of the exhaust fans 32, but almost all of the gases such as ozone produced inside the image forming apparatus 1 are removed by the filters when passing through the filters of the exhaust fans 32. However, a portion of the gases unable to be removed by the filters passes through the filters to be discharged outside. Causes for being unable to remove these gases include that it is difficult to sufficiently slow the current velocity of air that is exhausted by the exhaust fans 32 and also difficult to ensure a sufficient length of filter in the exhaust direction. It should be noted that in a case of sufficiently slowing the air flow, conflicting capabilities are necessary for sufficiently slowing the rotation of the exhaust fans 32 and producing a sufficient suction pressure for exhausting the air inside the image forming apparatus 1. Furthermore, ensuring a sufficient length of filter in the exhaust direction incurs a greater use of space in the image forming apparatus 1 and increases the apparatus size.

An air purifier 41 is a separate structure that is isolated from the ventilation device 31 and the printer portion 4 inside the image forming apparatus 1 and secluded from the atmosphere inside the image forming apparatus 1, and is arranged below the discharge tray 22 (see FIG. 1). In general, in the image forming apparatus 1 according to the present embodiment, the paper feeding cassettes 24 are arranged at the bottom portion of the image forming apparatus 1, the discharge tray 22 is arranged above the paper feeding cassettes 24, and the printer portion 4 is arranged at an intermediate height between the paper feeding cassettes 24 and the discharge tray 22, such that a space is provided below the discharge tray 22 (above the paper feeding cassettes 24 or adjacent to the printer portion 4), and the air purifier 41 is arranged in this space.

Although the installation space for the air purifier 41 is limited due to the compactness of the image forming apparatus 1, the above-described configuration easily enables an installation space for the air purifier 41 to be secured below the discharge tray 22.

Furthermore, by partitioning and arranging the air purifier 41 adjacent to the printer portion 4, it is easy to isolate it from the ventilation device 31 near the printer portion 4. With this configuration, it is possible to provide the ventilation device 31 and the air purifier 41 on the sides of the side wall portions 30a and 30c respectively, which are opposite each other in the main casing 30 of the image forming apparatus 1, and to provide the exhaust fans 32 of the ventilation device 31 and an intake port 43 of the air purifier 41 on the side wall portions 30a and 30c respectively.

The air purifier 41 has a casing 42, and the air purifier 41 is provided secluded from the atmosphere inside the image forming apparatus 1 due to this casing 42. The casing 42 of the air purifier 41 is L shaped when viewed from above (see FIG. 2), and both ends of this L shape are open to form an intake port 43 and an exhaust port 44. The intake port 43 is provided at the side wall portion 30c of the image forming apparatus 1, and the exhaust port 44 is provided at a front surface side wall portion 30d of the image forming apparatus 1.

In the casing 42 of the air purifier 41, a path of air is formed from the intake port 43 to the exhaust port 44, and a filter 45 is provided at the intake port 43, which is the inlet side of the air path, and an exhaust fan 46 and an ion generator 47 are provided midway on the air path.

The filter 45 is a commonly known activated carbon filter containing activated carbon, and suspended matter in the air that passes through the filter 45 is adsorbed to purify the air. For example, dust and mold and the like in the air are adsorbed and removed. Furthermore, chemical substances and the like such as silicone and the like can also be adsorbed and removed.

The ion generator 47 is a Plasmacluster ion (registered trademark) generating element (PCI). The PCI is provided with a positive ion generating portion that generates positive ions and a negative ion generating portion that generates negative ions, and both positive ions and negative ions are produced. This PCI is disclosed in detail in JP 2002-58731A, which was filed earlier by the applicant of the present invention.

In a same manner as the exhaust fans 32 of the ventilation device 31, the exhaust fan 46 is provided with a ventilation fan and a motor for rotationally driving the ventilation fan, and due to the rotational drive of the ventilation fan, an airflow is formed in which there is suction from the intake port 43 and discharge from the exhaust port 44.

The air purifier 41 operates in cooperation with the image forming apparatus 1 for example, and the motor of the exhaust fan 46 and the ion generator 47 are on during operation of the image forming apparatus 1, and motor of the exhaust fan 46 and the ion generator 47 are off during pauses of the image forming apparatus 1.

When the motor of the exhaust fan 46 turns on during operation of the image forming apparatus 1, the ventilation fan rotates such that air is suctioned from the intake port 43 and passes through the filter 45, then the air is discharged by the exhaust port 44 via the exhaust fan 46 and the ion generator 47. Furthermore, when the ion generator 47 turns on, the ion generator 47 generates positive ions and negative ions in the air.

At this time, in the air path inside the casing 42 of the air purifier 41, the filter 45 adsorbs and removes the suspended matter in the air to purify the air, and positive ions and negative ions are imparted to the air. Then, this air, which has been purified and imparted with positive ions and negative ions, is discharged outside by the exhaust port 44.

As described earlier, the exhaust port 44 of the air purifier 41 is provided at the front surface side wall portion 30d of the main casing 30 of the image forming apparatus 1. Furthermore, when the image forming apparatus 1 is installed, it is common to leave an open space at the front surface side of the image forming apparatus 1 (for example, on the side where the operation portion is provided). For this reason, the air discharged from the exhaust port 44 of the air purifier 41 readily spreads within a wide range of the room, and airborne microbes in the air within the room are efficiently removed by the positive ions and negative ions contained in this air.

In this way, in the image forming apparatus 1, inside the image forming apparatus 1 is ventilated by the ventilation device 31, thereby inhibiting rises in the internal temperature of the image forming apparatus 1. Furthermore, almost all the gases such as ozone and the like produced inside the image forming apparatus 1 are removed by the filters of the exhaust fans 32. Further still, the air is purified by the air purifier 41 and positive ions and negative ions are generated in the air, then the air is discharged outside by the exhaust port 44 to spread within a wide range of the room. And airborne microbes in the air within the room are efficiently removed by the positive ions and negative ions contained in this air.

Incidentally, not only is ozone produced in the electrophotographic image forming apparatus, but silicone mixed in the toner powder and release agents for releasing recording papers is vaporized, and this silicone sometimes disperses in the air. Although almost all this ozone and silicone is removed by the filters of the exhaust fans 32, a portion of these is unable to be removed and is discharged outside the image forming apparatus 1.

If this silicone-containing air is suctioned by the intake port 43 of the air purifier 41 and reaches the ion generator 47, the ion generating efficiency of the ion generator 47 will be undesirably reduced in a short period. This is considered to be because the silicone adheres to the discharging electrodes and the like of the ion generator 47, thereby reducing the insulation of the ion generator 47.

Accordingly, the image forming apparatus 1 according to the present embodiment is configured such that it is difficult for silicone to be suctioned by the intake port 43 of the air purifier 41, and even if silicone is suctioned by the intake port 43, this is removed by the filter so that silicone does not adhere to the discharging electrodes of the ion generator 47.

Specifically, the exhaust fans 32 of the ventilation device 31 and the intake port 43 of the air purifier 41 are provided in the side wall portions 30a and 30c respectively, which are opposite each other in the main casing 30 of the image forming apparatus 1. Thus, the exhaust fans 32 and the intake port 43 are separated sandwiching the main casing 30, and there is almost no direct flow of air from the exhaust fans 32 of the ventilation device 31 to the intake port 43 of the air purifier 41, and silicone discharged from the exhaust fans 32 is almost never suctioned by the intake port 43 of the air purifier 41.

Furthermore, the exhaust fans 32 of the ventilation device 31 are provided in a location higher than the intake port 43 of the air purifier 41. Air that is warmed inside the image forming apparatus 1 is discharged from the exhaust fans 32 of the ventilation device 31, and this warm discharged air rises outside the image forming apparatus 1. Accordingly, silicone discharged from the exhaust fans 32 of the ventilation device 31 is almost never suctioned into the intake port 43 of the air purifier 41, which is lower than the exhaust fans 32.

In this way, the exhaust fans 32 of the ventilation device 31 and the intake port 43 of the air purifier 41 are provided on the side wall portions 30a and 30c respectively, which are opposite each other in the main casing 30 of the image forming apparatus 1, and the exhaust fans 32 of the ventilation device 31 are provided in a location higher than the intake port 43 of the air purifier 41. As a result, the silicone that is discharged from the exhaust fans 32 of the ventilation device 31 is almost never suctioned into the intake port 43 of the air purifier 41, which prevents the silicone from adhering to the discharging electrodes of the ion generator 47 and enables the ion generating efficiency of the ion generator 47 to be maintained over a long period.

Furthermore, although a small amount of silicone is suctioned into the intake port 43 of the air purifier 41 since the silicone that is discharged from the exhaust fans 32 of the ventilation device 31 is dispersed into the air of the room, this small amount of silicone is removed by the filter 45 of the intake port 43, and therefore due to this also, the silicone is prevented from adhering to the discharging electrodes of the ion generator 47 and the ion generating efficiency of the ion generator 47 is maintained without dropping. Accordingly, the filter 45 fulfills two roles of purifying the air and preventing reductions in the ion generating efficiency of the ion generator 47.

Further still, as described earlier, the ventilation device 31 and the air purifier 41 are provided near the side wall portions 30a and 30c respectively, which are opposite each other in the main casing 30 of the image forming apparatus 1, and since the exhaust fans 32 of the ventilation device 31 and the intake port 43 of the air purifier 41 are provided on the side wall portions 30a and 30c respectively, the intake port 43 is far from the exhaust fans 32, and therefore it is not necessary to lengthen the casing 42 of the air purifier 41, and it is not necessary to increase the size of the air purifier 41, and thus increases in size of the image forming apparatus 1 can be inhibited.

It should be noted that the air purifier 41 and the image forming apparatus 1 are operated in cooperation, but it is also possible to turn on and off the air purifier 41 by operating a power switch thereof, thus operating it independently from the image forming apparatus 1.

Figure 3:
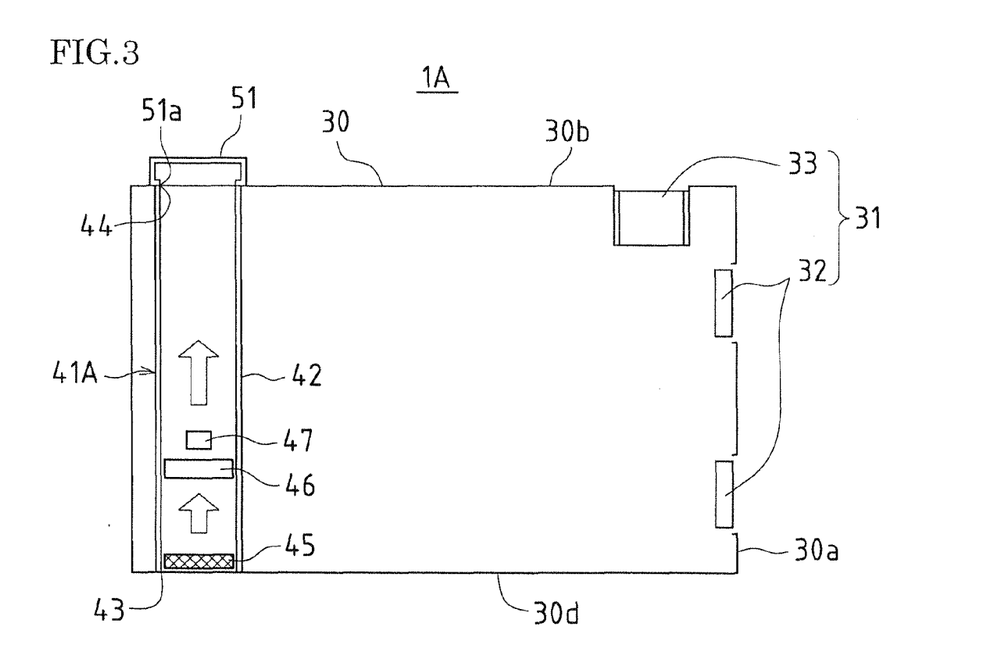
FIG. 3 is a schematic view showing a ventilation device and an air purifier in an image forming apparatus as viewed from above in a second embodiment of an image forming apparatus according to the present invention.
Figure 4:
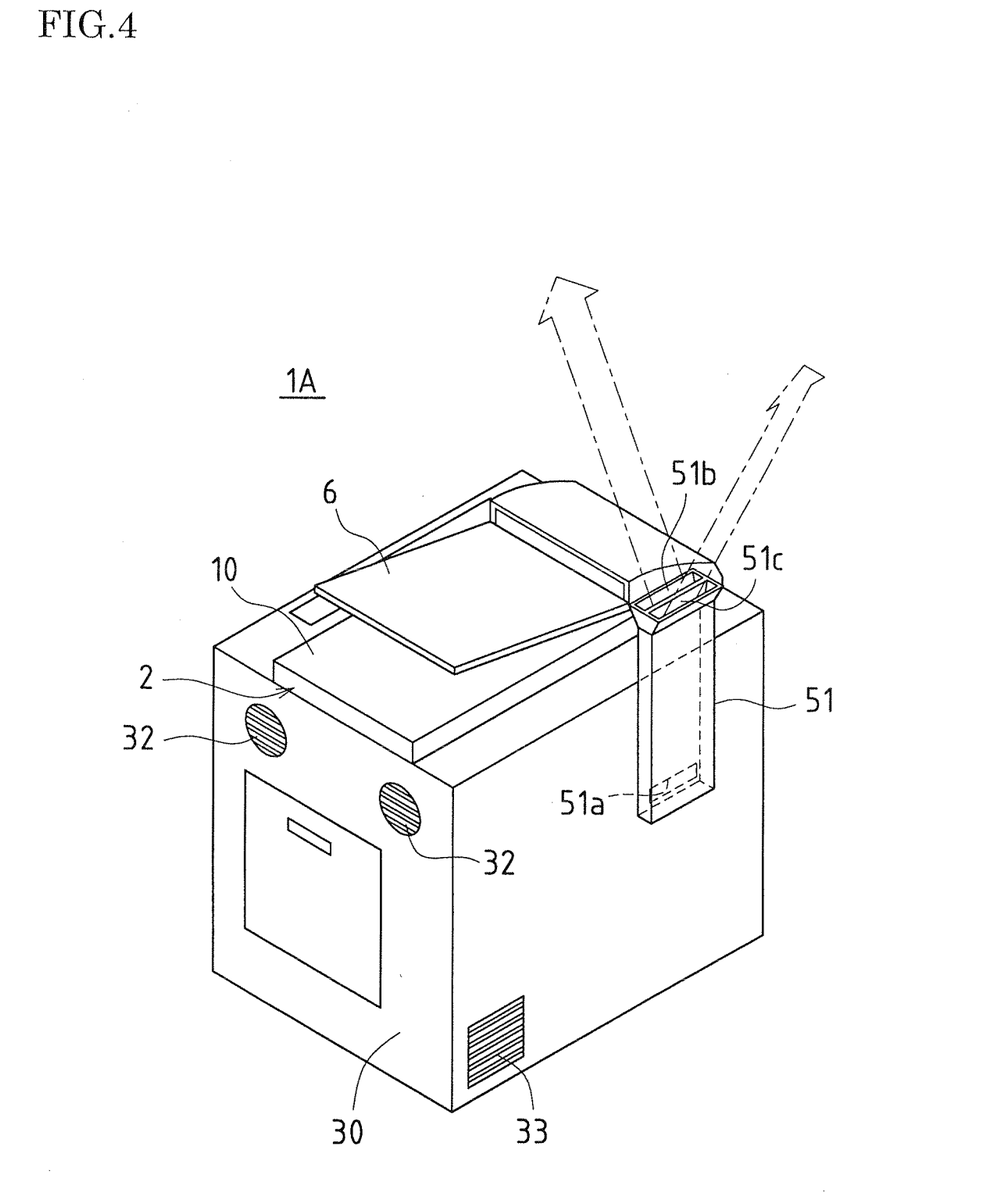
FIG. 4 is a perspective view showing the image forming apparatus of FIG. 3.
Figure 5:
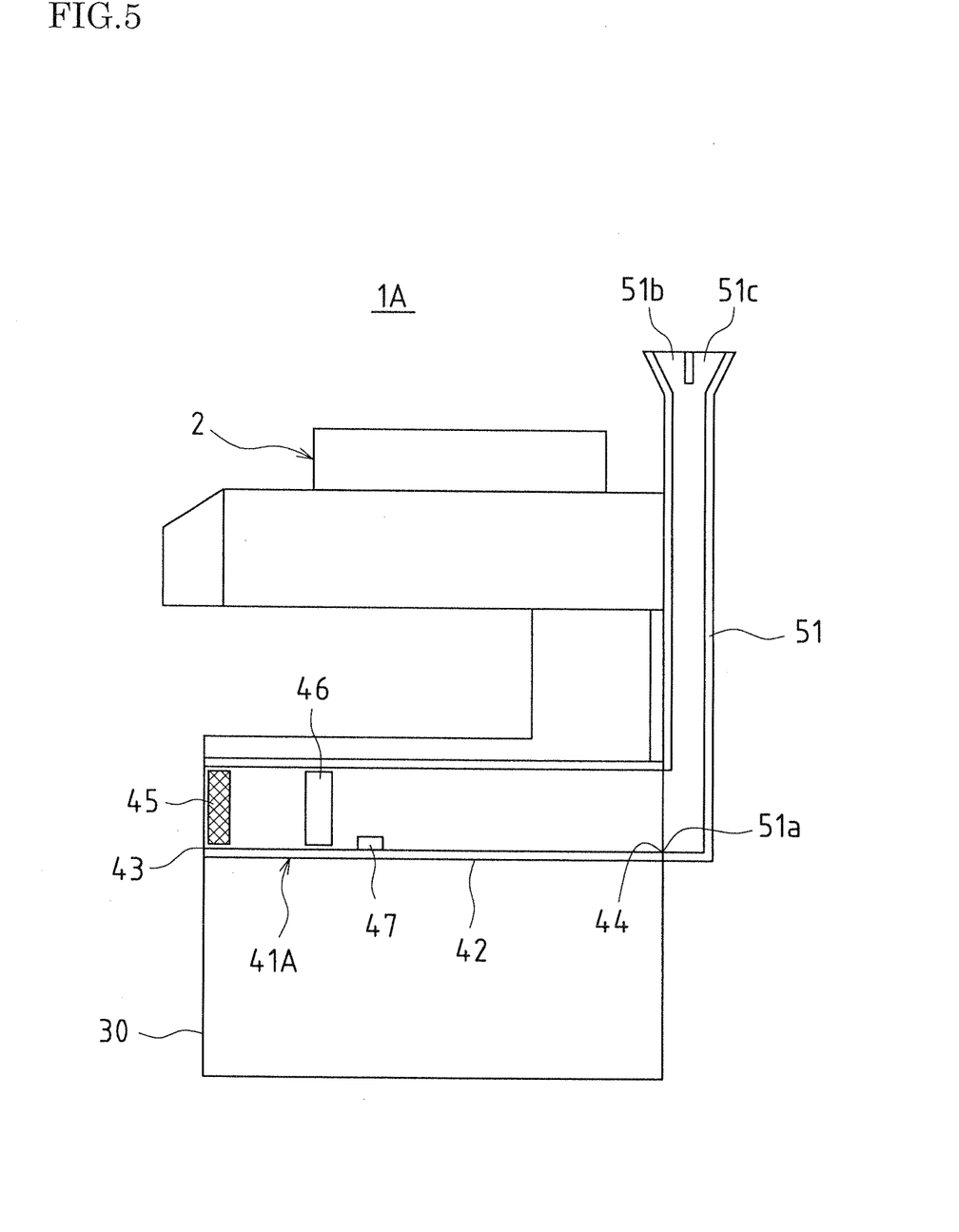
FIG. 5 is a cross-sectional view showing the image forming apparatus of FIG. 3.

FIG. 3 is a schematic view showing a second embodiment of an image forming apparatus according to the present invention as viewed from above. Furthermore, FIG. 4 is a perspective view showing an image forming apparatus according to the present embodiment. Further still, FIG. 5 is a cross-sectional view showing an image forming apparatus according to the present embodiment. It should be noted that in FIGS. 3 to 5, same reference symbols are assigned to portions that fulfill a same function as the apparatus in FIG. 1 and FIG. 2.

In a same manner as the image forming apparatus 1 of FIG. 1 and FIG. 2, an image forming apparatus 1A according to the present embodiment is provided with the original transport portion 2, the original reading portion 3, the printer portion 4, and the paper feeding portion 5, and the layout thereof is unchanged. Furthermore, the ventilation device 31 is provided and the layout of the exhaust fans 32 and the intake port 33 is also unchanged. However, instead of the air purifier 41 of FIG. 1 and FIG. 2, an air purifier 41A and a duct 51 are applied.

A casing 42 of the air purifier 41A is a tubular cuboid, and ends thereof form an intake port 43 and an exhaust port 44. The intake port 43 is provided at the front surface side wall portion 30d of the main casing 30, and the exhaust port 44 is provided at the rear surface side wall portion 30b of the main casing 30.

In the casing 42 of the air purifier 41A, a filter 45 is provided at the intake port 43, which is the inlet side of the air path, and an exhaust fan 46 and an ion generator 47 are provided midway on the air path. When the exhaust fan 46 turns on, air is suctioned from the intake port 43 and passes through the filter 45, then the air is discharged by the exhaust port 44 via the exhaust fan 46 and the ion generator 47.

The duct 51 is tubular and its bottom portion is closed, with a connecting port 51a provided at a side wall thereof, and this connecting port 51a overlays and connects to an exhaust port 44 of the casing 42 of the air purifier 41A. Furthermore, the duct 51 extends upward higher than the image forming apparatus 1A, with its top end having two exhaust ports 51b and 51c.

Here, when the exhaust fan 46 of the air purifier 41A turns on, air is suctioned from the intake port 43 and discharged by the exhaust port 44. This air is guided within the duct 51 from the exhaust port 44 through the connecting port 51a of the duct 51, then guided upward through the duct 51 to be discharged from the two exhaust ports 51b and 51c at the top end of the duct 51. One of the exhaust ports, the exhaust port 51b, is an opening for air to be discharged upward at the front surface side of the image forming apparatus 1A, and the other exhaust port, the exhaust port 51c, is an opening for air to be discharged upward at the rear surface side of the image forming apparatus 1A.

Accordingly, air discharged from the air purifier 41A is released in two directions, front upward and rear upward of the image forming apparatus 1A, such that it spreads wider within the room. And airborne microbes in the air within the room are efficiently removed by the positive ions and negative ions contained in this air.

Furthermore, the intake port 43 of the air purifier 41A is provided at the front surface side wall portion 30d of the main casing 30 apart from the exhaust fans 32 of the ventilation device 31 at the right side wall portion 30a of the main casing 30, and is positioned lower than the exhaust fans 32. For this reason, silicone discharged from the exhaust fans 32 is almost never suctioned into the intake port 43 of the air purifier 41A.

Further still, even if a small amount of silicone is suctioned into the intake port 43 of the air purifier 41A since the silicone that is discharged from the exhaust fans 32 is dispersed into the air of the room, this small amount of silicone is removed by the filter 45 of the intake port 43.

Figure 6:
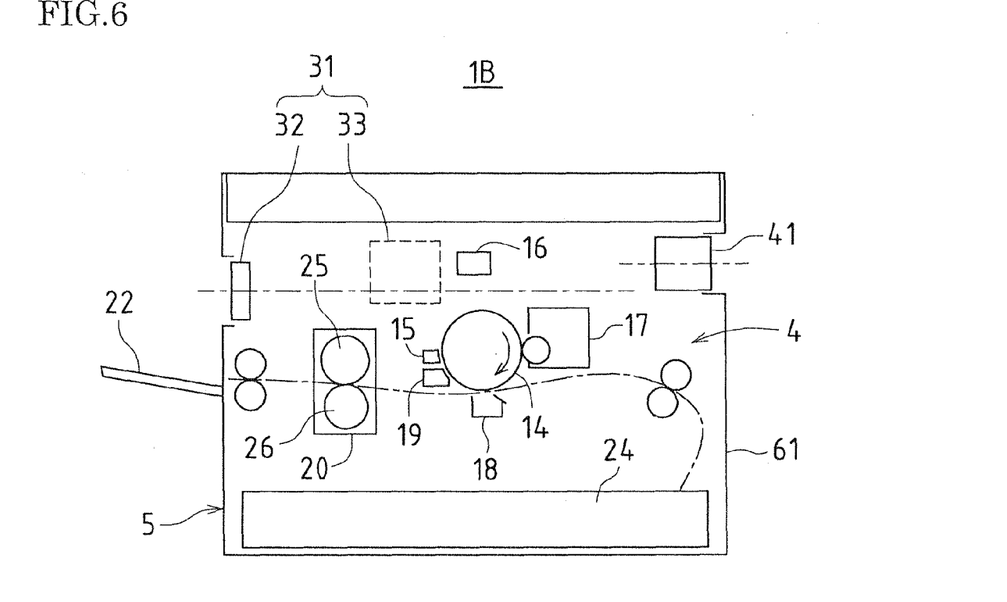
FIG. 6 is a cross-sectional view that schematically shows a third embodiment of an image forming apparatus according to the present invention.

FIG. 6 is a cross-sectional view that schematically shows a third embodiment of an image forming apparatus according to the present invention. It should be noted that in FIG. 6, same reference symbols are assigned to portions that fulfill a same function as the apparatus in FIG. 1 and FIG. 2.

An image forming apparatus 1B according to the present embodiment is a printer that obtains image data received externally, and forms a monochrome image indicated by the image data on a recording paper, and its structure can be broadly divided into a printer portion 4 and a paper feeding portion 5.

The printer portion 4 is arranged above the paper feeding portion 5 and is provided with a photosensitive drum 14, a charging unit 15, an optical scanning unit 16, a developer unit 17, a transfer unit 18, a cleaning unit 19, and a fixing device 20. When a recording paper is transported from the paper feeding portion 5 to the printer portion 4, the recording paper passes between the photosensitive drum 14 and the transfer unit 18, then a toner image on the surface of the photosensitive drum 14 is transferred to the recording paper, and the toner image is fixed onto the recording paper by the fixing device 20, then the recording paper is discharged to a discharge tray 22.

The paper feeding portion 5 is arranged at a bottom portion of the image forming apparatus 1B, and recording papers are withdrawn sheet by sheet from a paper feeding cassette 24 thereof and transported and fed to the printer portion 4.

Figure 7:
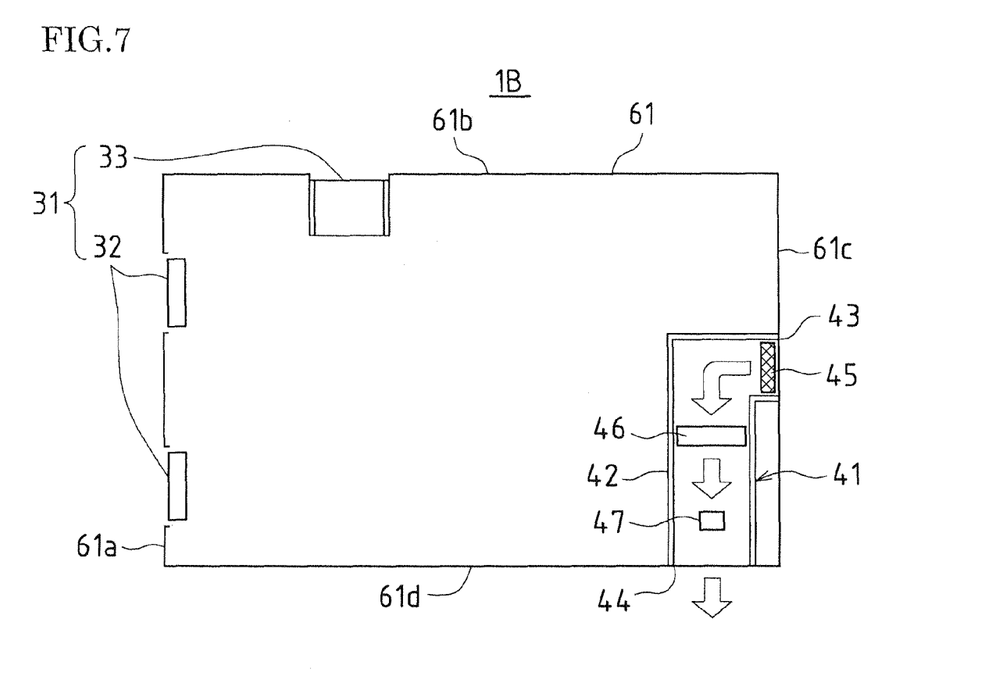
FIG. 7 is a schematic view showing a ventilation device and an air purifier in an image forming apparatus as viewed from above in the image forming apparatus of FIG. 6.

FIG. 7 is a schematic view showing a ventilation device and an air purifier in the image forming apparatus 1B as viewed from above. The image forming apparatus 1B has a main casing 61, which is a substantially six sided solid shape. A ventilation device 31 is provided with two exhaust fans 32, which are arranged on a left side wall portion 61a of the main casing 61, and an intake opening 33, which is arranged on a rear surface side wall portion 61b of the main casing 61.

The exhaust fans 32 fulfill a function of exhaust ports that forcibly discharge air within the image forming apparatus 1B, and are disposed near and above the fixing device 20 (see FIG. 6) so as to be capable of efficiently exhausting hot air that rises from near the heating roller 25 of the fixing device 20.

Furthermore, the intake port 33 is a simple opening formed in the rear surface side wall portion 61b of the main casing 61. The intake port 33 is positioned such that the fixing device 20 is sandwiched between the exhaust fans 32 and the intake port 33, and outside air that is suctioned from here reaches the exhaust fans 32 through the fixing device 20.

For example, when the internal temperature of the image forming apparatus 1B exceeds a fixed value during operation of the image forming apparatus 1B, the motors of the exhaust fans 32 are rotationally driven. Due to the rotational drive of the motors of the exhaust fans 32, their ventilation fans rotate and discharge the air inside the image forming apparatus 1B, while on the other hand, outside air is suctioned from the intake port 33 into the image forming apparatus 1B, thereby ventilating inside the image forming apparatus 1B. As a result, rises in the internal temperature of the image forming apparatus 1B are inhibited. It should be noted that when the internal temperature of the image forming apparatus 1B falls below the fixed value, the motors of the exhaust fans 32 are stopped.

The air purifier 41 is a separate structure that is isolated from the ventilation device 31 and the printer portion 4 inside the image forming apparatus 1B, and is arranged at a right side of the main casing 61 of the image forming apparatus 1B.

The air purifier 41 has an L shaped casing 42 that forms an air path, and the air purifier 41 is provided secluded from the atmosphere inside the image forming apparatus 1B due to this casing 42. The intake port 43 and the exhaust port 44 of the ends of the L shaped casing 42 are provided at the right side wall portion 30c and front surface side wall portion 61d of the main casing 61 of the image forming apparatus 1B.

In the casing 42 of the air purifier 41, a filter 45 is provided at the intake port 43, and an exhaust fan 46 and an ion generator 47 are provided between from the intake port 43 and the exhaust port 44.

The exhaust fan 46 forms an airflow of suctioning from the intake port 43 and discharging from the exhaust port 44.

When the motor of the exhaust fan 46 in the air purifier 41 turns on, air is suctioned from the intake port 43 and passes through the filter 45, then the air is discharged by the exhaust port 44 via the exhaust fan 46 and the ion generator 47.

At this time, the filter 45 adsorbs and removes the suspended matter in the air to purify the air, and the ion generator 47 generates positive ions and negative ions in the air, then this air, which has been purified and imparted with positive ions and negative ions, is discharged outside by the exhaust port 44.

Since the exhaust port 44 of the air purifier 41 is arranged at the front surface side wall portion 61d of the main casing 61 of the image forming apparatus 1B, the air discharged from the exhaust port 44 of the air purifier 41 readily spreads within a wide range of the room, and airborne microbes in the air within the room are efficiently removed by the positive ions and negative ions contained in this air.

Here, with the image forming apparatus 1B, although the ozone and silicone produced in the image forming apparatus 1B is removed by the filters of the exhaust fans 32, a portion of these is unable to be removed and is discharged outside the image forming apparatus 1.

Accordingly, the image forming apparatus 1B according to the present embodiment is configured such that it is difficult for silicone to be suctioned by the intake port 43 of the air purifier 41, and even if silicone is suctioned by the intake port 43, this is removed by the filter. Specifically, the exhaust fans 32 of the ventilation device 31 and the intake port 43 of the air purifier 41 are provided in the side wall portions 61a and 61c respectively, which are opposite each other in the main casing 61 of the image forming apparatus 1B. Thus, the exhaust fans 32 and the intake port 43 are separated sandwiching the main casing 61, and air discharged from the exhaust fans 32 of the ventilation device 31 is almost never suctioned by the intake port 43 of the air purifier 41.

Accordingly, the silicone that is discharged from the exhaust fans 32 of the ventilation device 31 is almost never suctioned into the intake port 43 of the air purifier 41, which prevents the silicone from adhering to the discharging electrodes of the ion generator 47 and enables the ion generating efficiency of the ion generator 47 to be maintained over a long period without dropping.

Furthermore, even if a small amount of silicone is suctioned into the intake port 43 of the air purifier 41 after the silicone that is discharged from the exhaust fans 32 of the ventilation device 31 is dispersed into the air of the room, this small amount of silicone is removed by the filter 45 of the intake port 43, and therefore due to this also, the silicone is prevented from adhering to the discharging electrodes of the ion generator 47 and the ion generating efficiency of the ion generator 47 is prevented from dropping.

Figure 8:
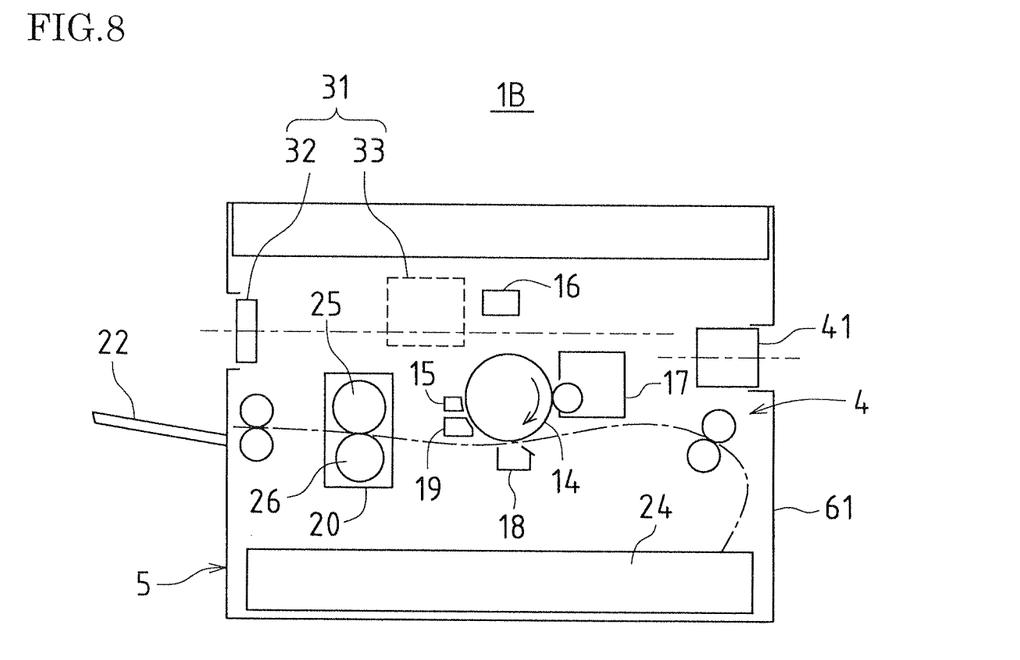
FIG. 8 is a cross-sectional view that schematically shows a modified example of the image forming apparatus of FIG. 6 and FIG. 7.

FIG. 8 is a cross-sectional view that schematically shows a modified example of the image forming apparatus 1B of FIG. 6 and FIG. 7.

In a same manner as the image forming apparatus 1B of FIG. 6 and FIG. 7, an image forming apparatus 1B according to this modified example is provided with the printer portion 4 and the paper feeding portion 5, and the layout thereof is unchanged. Furthermore, the ventilation device 31 is provided and the layout of the exhaust fans 32 and the intake port 33 is also unchanged. Further still, although there is no change in that the air purifier 41 is provided, the air purifier 41 in the image forming apparatus 1B of FIG. 6 and FIG. 7 is moved (arranged) lower.

By moving the air purifier 41 lower, the positions of the exhaust fans 32 of the ventilation device 31 become higher than the intake port 43 of the air purifier 41. Air that is warmed inside the image forming apparatus 1B is discharged from the exhaust fans 32 of the ventilation device 31, and this warm air rises outside the image forming apparatus 1B, and therefore silicone discharged from the exhaust fans 32 of the ventilation device 31 is almost never suctioned into the intake port 43 of the air purifier 41, which is lower than the exhaust fans 32, such that silicone tends not to adhere to the discharging electrodes of the ion generator 47.

Embodiments of the present invention are described above in detail, but the present invention is not limited to the above-described embodiments, and design modifications and the like that do not depart from the gist of the present invention are included within the scope of the present invention.

For example, it is also possible to provide the exhaust fans 32 and the intake port 43 in side wall portions that sandwich a single corner, that is, in the right side wall portion or the left side wall portion and the front surface side wall portion and the rear surface side wall portion. In this case also, the intake port 43 can be set reliably apart from the exhaust fans 32 such that the silicone discharged from the exhaust fans 32 is not suctioned into the intake port 43.

Furthermore, it is also possible to provide the exhaust fans 32 and the intake port 43 at a single side wall portion of the main casing apart from each other below and above. The air discharged from the exhaust fans 32 rises outside the image forming apparatus, and therefore if the exhaust fans 32 are arranged above the intake port 43, then almost no silicone discharged from the exhaust fans 32 is suctioned into the intake port 43.

Further still, even by merely providing the exhaust fans 32 and the intake port 43 apart from each other at a single side wall portion of the main casing at upper and lower end portion positions or left and right end portion positions, the silicone discharged from the exhaust fans 32 can be inhibited from being suctioned into the intake port 43.

Furthermore, the exhaust fans 32 and the intake port 33 of the ventilation device 31 are provided as illustrations, but a component constituted by a simple exhaust port and intake port is also possible. As long as the exhaust port is arranged above the intake port, an airflow is created in which outside cold air flows into the main casing from the intake port, then this air is warmed inside the main casing and rises, and the air is discharged from the exhaust port, and therefore even with only a simple exhaust port and intake port, ventilation is possible for inside the main casing.

What is claimed is:

1. An image forming apparatus, comprising:
    a ventilation device that ventilates air inside the image forming apparatus, the ventilation device including an intake port and at least one exhaust port; and
    an air purifier having an ion generator that is provided in an isolated manner inside the image forming apparatus, the air purifier comprising a purifier duct that isolates air passing through the air purifier from air located inside the image forming apparatus, wherein air outside the image forming apparatus is suctioned and purified by the air purifier, with purified air being discharged, and an intake port of the air purifier that suctions air is provided in a location apart from an exhaust port of the ventilation device.

2. The image forming apparatus according to claim 1, wherein the intake port of the air purifier and the at least one exhaust port of the ventilation device are provided in mutually different wall portions, respectively, of a main casing of the image forming apparatus.

3. The image forming apparatus according to claim 2, wherein the intake port of the air purifier and the at least one exhaust port of the ventilation device are provided in wall portions, respectively, that are opposite each other of the main casing of the image forming apparatus.

4. The image forming apparatus according to claim 2, wherein the intake port of the air purifier and the at least one exhaust port of the ventilation device are provided in a front surface side wall portion and a rear surface side wall portion, respectively, of the main casing of the image forming apparatus.

5. The image forming apparatus according to claim 1, wherein the intake port of the air purifier and the at least one exhaust port of the ventilation device are provided apart from each other below and above, respectively, a center portion of the main casing of the image forming apparatus.

6. The image forming apparatus according to claim 1, wherein an exhaust port of the air purifier is provided at a front surface side wall portion of a main casing of the image forming apparatus.

7. The image forming apparatus according to claim 1, wherein a discharge duct is provided that protrudes above the image forming apparatus, and an exhaust port of the air purifier that discharges air is connected to the discharge duct to discharge air via the duct to above the image forming apparatus.

8. The image forming apparatus according to claim 1, comprising:
    a paper feeding portion arranged at a bottom portion of the image forming apparatus,
    a paper discharge portion arranged above the paper feeding portion, and
    a printer portion that is arranged at an intermediate height between the paper feeding portion and the paper discharge portion, and that receives a recording paper from the paper feeding portion and forms an image on the recording paper, then discharges the recording paper to the paper discharge portion, wherein the air purifier is arranged below the paper discharge portion.

9. The image forming apparatus according to claim 1, wherein the air purifier is provided with a filter for adsorbing silicone.

10. The image forming apparatus according to claim 7, wherein a discharge end of the discharge duct is positioned above a top surface of the main casing of the image forming apparatus.

11. The image forming apparatus according to claim 10, wherein the discharge end of the discharge duct includes a plurality of exhaust ports that direct air exiting the duct in a corresponding plurality of different directions.

12. The image forming apparatus according to claim 1, wherein the intake port and at least one exhaust port of the ventilation device and the intake port and an exhaust port of the air purifier are all located on separate sidewalls of a main casing of the image forming apparatus.

* * * * *